United States Patent [19]
Lundstrom et al.

[11] Patent Number: 5,433,208
[45] Date of Patent: Jul. 18, 1995

[54] DEVICE FOR FILTERING OUT BASELINE FLUCTUATIONS FROM PHYSIOLOGICAL MEASUREMENT SIGNALS

[75] Inventors: Lena Lundstrom; Peter Karlsson, both of Stockholm; Thomas Ohlsson, Vallingby, all of Sweden

[73] Assignee: Siemens Aktiengesellschaft, Munich, Germany

[21] Appl. No.: 117,067
[22] PCT Filed: Mar. 4, 1992
[86] PCT No.: PCT/EP92/00474
  § 371 Date: Dec. 22, 1993
  § 102(e) Date: Dec. 22, 1993
[87] PCT Pub. No.: WO92/15243
  PCT Pub. Date: Sep. 17, 1992

[30] Foreign Application Priority Data
Mar. 1, 1991 [DE] Germany .................. 41 06 858.0

[51] Int. Cl.⁶ .............................................. A61N 5/04
[52] U.S. Cl. .................................................. 128/696
[58] Field of Search ............................ 128/630, 696

[56] References Cited

U.S. PATENT DOCUMENTS

| | | | |
|---|---|---|---|
| 4,317,094 | 2/1982 | Potter | 333/165 |
| 4,472,785 | 9/1984 | Kasuga | 364/718 |
| 4,896,152 | 1/1993 | Tiemann | 340/843 |
| 5,042,026 | 8/1991 | Koike et al. | 370/32.1 |

FOREIGN PATENT DOCUMENTS

| | | |
|---|---|---|
| 3007907 | 9/1981 | Germany . |
| 210148 | 5/1984 | Germany . |
| 3047450 | 7/1985 | Germany . |
| 3028705 | 7/1987 | Germany . |
| 3916236 | 11/1990 | Germany . |
| 2209648 | 9/1987 | United Kingdom . |

OTHER PUBLICATIONS

*Journal of Clinical Engineering*, vol. 7, No. 3, Jul.–Sep. 1982 entitled "Digital FIR Filtering of ECG Baseline Wander" by J. P. Marques De Sa, pp. 235–240.

*IEEE Transactions on Biomedical Engineering*, vol. BME-32, No. 12, Dec. 1985, entitled "Removal of Base-Line Wander and Power-Line Interference from the ECG by an Efficient FIR Filter with a Reduced Number of Taps", by J. A. Van Alsté, Member, IEEE and T. S. Schilder, pp. 1052–1060.

*Primary Examiner*—William E. Kamm
*Attorney, Agent, or Firm*—Hill, Steadman & Simpson

[57] ABSTRACT

Apparatus for filtering out baseline fluctuations from physiological measurement signals. The apparatus comprises a first nonrecursive low-pass filter with a downstream stage for the reduction of the sampling rate, a second nonrecursive filter connected thereto, a subsequent interpolation stage to increase the sampling rate and a subtraction stage, in which the baseline fluctuations retained by the low-pass filtering are subtracted from the measurement signals affected by baseline fluctuations. To reduce the number of computing operations to be performed in the course of the sampling filtering, the first low-pass filter comprises a recursive filter.

2 Claims, 2 Drawing Sheets

DEVICE FOR FILTERING OUT BASELINE FLUCTUATIONS FROM PHYSIOLOGICAL MEASUREMENT SIGNALSa1

BACKGROUND OF THE INVENTION

1. Field Of the Invention

The invention relates to a device for filtering out baseline fluctuations from physiological measurement signals, comprising a sampling stage for the formation of sampled values of the measurement signals, a first low-pass filter connected thereto, a downstream stage for the reduction of the sampling rate by a predetermined factor, a subsequent nonrecursive second low-pass filter, a subsequent interpolation stage for increasing the sampling rate by the predetermined factor and a subtraction stage for the subtraction of the sampled values coming from the interpolation stage from the sampled values of the physiological measurement signal, coming from the sampling stage.

2. Description of the Related Art

Physiological measurement signals which are taken from patients are normally overlaid by disturbance signals such as, for example, the 50 Hz (60 Hz in the United States) alternating voltage induced by the alternating current grid, electrical muscle potentials and artifacts in conjunction with the taking of the physiological measurement signals from the patient. These disturbances are expressed, to the extent that they are of low-frequency type in comparison with the characteristic frequency of the physiological measurement signals, in the form of baseline fluctuations in the recorded measurement signal progression.

"Journal of Clinical Engineering", vol. 7, No. 3, July-September 1982, pages 235–240, discloses a device of the abovementioned type for filtering out baseline fluctuations from an electrocardiogram. In the disclosure, the baseline fluctuations are filtered out from the electrocardiogram signals in a high-pass filter which comprises a first nonrecursive low-pass filter with a downstream stage for the reduction of the sampling rate by the factor 8, a second nonrecursive low-pass filter connected thereto, a subsequent interpolation stage for increasing the sampling rate by the factor 8 and a subtraction stage, in which the baseline fluctuations obtained as a result of the low-pass filtering are subtracted from the electrocardiographic signal affected by the baseline fluctuations. As a result of the use of nonrecursive (FIR) filters having a pulse response with a limited number of pulses (finite impulse response), phase shifts and thus signal distortions in the filtering are avoided. However, the computing effort, i.e. the number of computing operations to be performed in the filter (multiplications) is very great in the case of nonrecursive filters, thus the sapling rate of the electrocardiogram is reduced by the factor 8, before the electrocardiographic signal is fed to the second nonrecursive low-pass filter. In this case, the first low-pass filter serves for the frequency limitation of the electrocardiogram, that is required for the reduction of the sampling rate. The greater the reduction factor, the smaller the computing effort in the case of the second nonrecursive filter, but at the same time the computing effort in the case of the first nonrecursive filter increases. Accordingly, in the case of the known device, there is provided, ahead of the actual baseline filtering, a prefiltering with a reduction of the sampling rate by the factor 2. As a result of this the resolution of the electrocardiographic signal in toto is reduced.

SUMMARY OF THE INVENTION

It is an object of the present invention of filtering out of baseline fluctuations from physiological measurement signals to reduce the required computing effort.

The object of the present invention is inventively achieved in an apparatus having the first low-pass filter that is a recursive filter, the cutoff frequency of which is selected in relation to the cutoff frequency of the second low-pass filter so that the frequency range of phase shifts caused by the first low-pass filter are filtered out in the second low-pass filter. In comparison with nonrecursive filters, recursive filters are indeed distinguished by a lower computing effort in relation to the filter performance or filter action. The disadvantage of recursive filters causing phase shifts in the signal to be filtered does not occur in the case of the apparatus of the invention since the frequency range of the phase shifts is filtered out in the second low-pass filter.

A reduction of signal distortions in the filtering is advantageously achieved in the present invention by a retardation stage for the retarded onward transmission of the sampled values coming from the sampling stage to the subtraction stage. In this case, for the retardation stage the same retardation is selected as is the case in the low-pass filters.

On account of the reduced computing effort in the filtering, the apparatus of the invention is advantageously used in the process-coupled, (i.e. on-line analysis) of the physiological signals.

BRIEF DESCRIPTION OF THE DRAWINGS

The exemplary embodiment of an apparatus for filtering out baseline fluctuations from physiological measurement signals of the present invention shall be set forth in greater detail below with reference to the figures.

DESCRIPTION OF THE PREFERRED EMBODIMENTS

Figure 1:
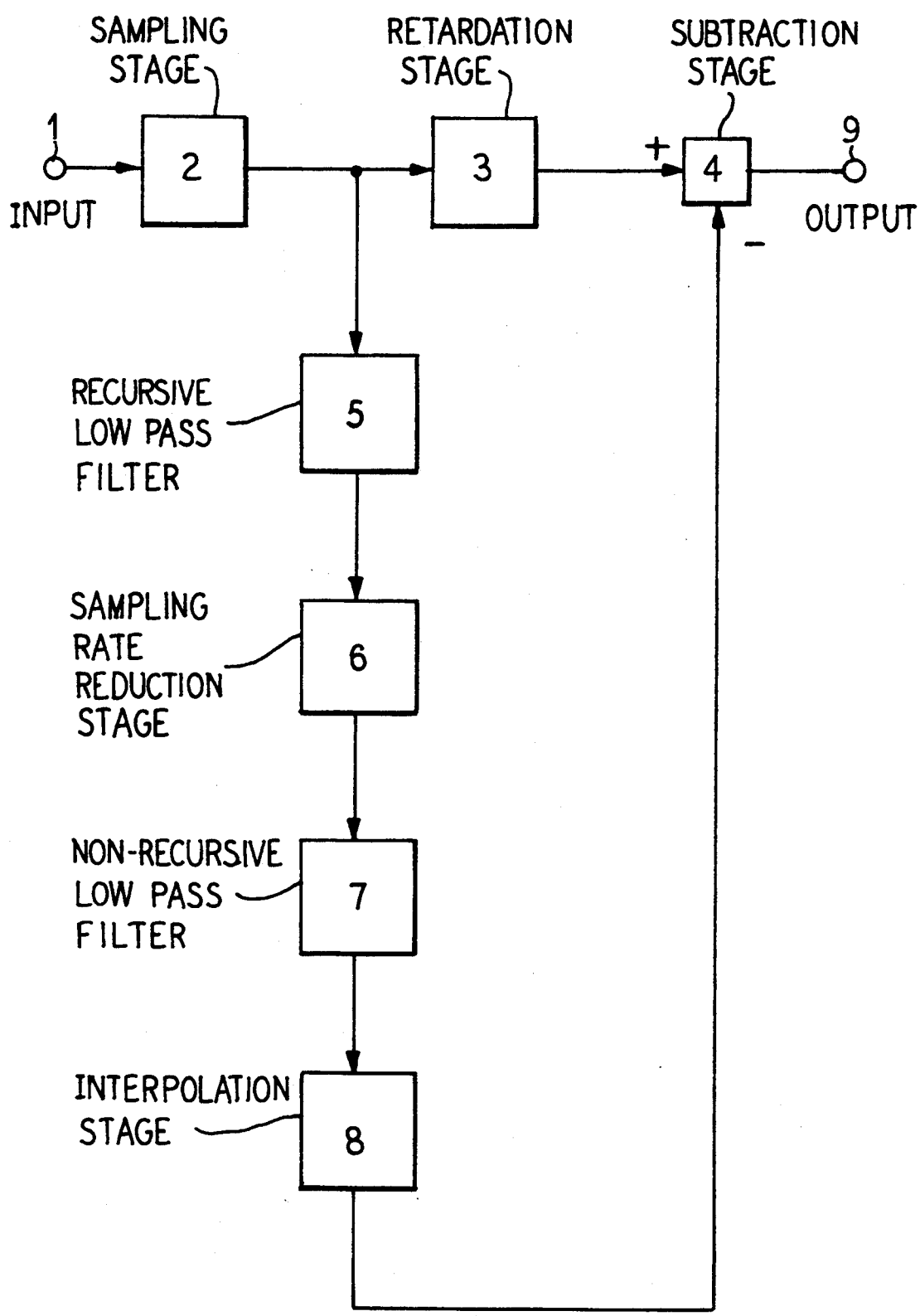
FIG. 1 shows an illustrative embodiment of the apparatus of the present invention in the form of a block diagram.

The reference symbol 1 designates an input of the apparatus having a physiological measurement signal, for example an electrocardiographic signal taken from a patient. A sampling stage 2 for the formation of sampled values of the physiological signal connects to the input 1. The sampled values are, on the one hand, connected via a retardation stage 3 to a first input (+) of a subtraction stage 4 and on the other hand via a first low-pass filter 5, a sampling rate reduction stage 6 for the reduction of the sampling rate, a subsequent second low-pass filter 7 and an interpolation stage 8 connected thereto, to a second input (−) of the subtraction stage 4. The output, 9 the physiological measurement signal cleared of the baseline fluctuations, is available in the form of sampled values for further process-coupled (on-line) signal processing. In the units 5 to 8, the sampled physiological measurement signal is low-pass-filtered, so that at the second input (−) of the subtraction stage 4, the sampled values of the baseline fluctuations appear. These values are subtracted in the substraction stage 4 from the sampled values of the physiological measurement signal. The units 3 to 8 thus form a high-pass filter.

Each of the sampling stage 2, the retardation stage 3, the low pass filter 5, the sampling rate reductions stage 6, the low pass filter 7 and the interpolation stage 8 are individually circuits, or combinations of circuits, which are known to those of ordinary skill in the art. Suitable circuitry for constructing each of these aforementioned elements, for example, is disclosed in the text "Introduction To Digital Signal Processing," Proakis et al., Macmillan Publishing Co. (1989). The teachings of this text are incorporated herein by reference. Suitable circuitry for these sampling stage 2 is disclosed in chapter 4.5 of that text, circuitry for the low pass filter 5 (which, as discussed below, may be a recursive filter) is disclosed in chapters 7.3 and 8.2, circuitry for the sampling rate reduction stage 6 is disclosed in chapter 8.5, circuitry for the low pass filter 7 (which, as discussed below, may be a non-recursive filter) is discussed in chapters 7.2 and 8.1, and circuitry for the interpolation stage 8 is disclosed in chapter 8.5. The retardation stage 3 identified above is a standard relay circuit of the type well known to those of ordinary skill in the art, and the substraction stage 4 is also a standard circuit known to those skilled in the art.

The low-pass filter designated by 7 is a nonrecursive filter which generates no phase errors in the course of the filtering. However, (the computing effort, i.e. the number of computing operations to be performed) and the signal retardation are relatively great in such filters. In order to reduce both of these, the rate of sampled values which is fed to the low-pass filter 7 is reduced. This is possible on account of the relatively low frequency of the baseline fluctuations. The reduction of the sampling rate takes place in the stage 6. The low-pass filter 5 which is disposed ahead of the stage 6 serves for the frequency limitation of the sampled measurement signal. This frequency limitation is required for the reduction of the sampling rate. The sampling rate reduction stage 6 reduces the sampling rate by selecting every $n^{th}$ sample and discards the other $(n-1)$ samples. In an embodiment, the sampling rate reduction stage 6 selects every $12^{th}$ sample and discards the other 11 samples. In contrast to the second filter 7, the first filter 5 is a recursive filter, having a computing effort the considerably lower in relation to the filter performance. The disadvantage of the recursive filter 5 causing phase errors in the signal to be filtered does not appear, since the cutoff frequency of the filter 5 is selected dependent upon the filter 7 so that the phase errors are filtered out in the filter 7. An interpolation stage 8 is an interpolation stage of a known type, for example, a linear interpolation stage. The interpolation stage 8 merely returns the sampling rate to that rate which was used before the rate was reduced by the specific factor used in the sampling rate reduction stage 6.

Since the low-pass filtering in the units 5 to 8 takes place with a specified retardation, the unfiltered sampled measurement signal is retarded in parallel therewith in the retardation stage 3 by the same amount. This permits, in the subtraction stage 4, a subtraction, free from errors on account of retardation differences, of the baseline fluctuations from the measurement signal.

In the case of the illustrative embodiment shown for filtering out baseline fluctuations from an electrocardiogram, a sampling rate in the sampling stage 2 of 500 Hz is preferably provided; the reduction factor in the sampling rate reduction stage 6 is 40. The device operates in a process-coupled manner (on-line) with a signal processor, only a fraction of the computing capacity of which is required for the filtering.

Figure 2:
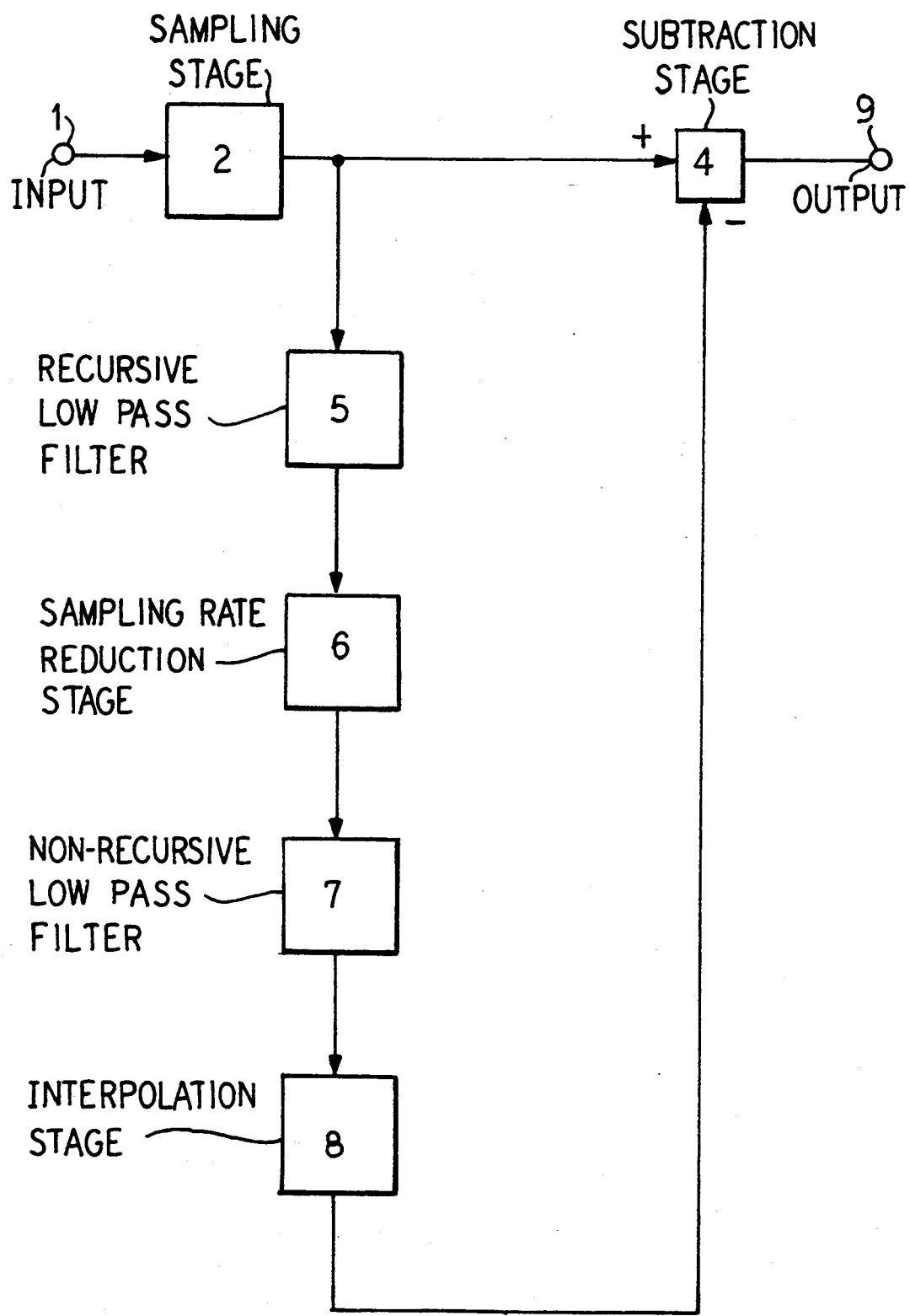
FIG. 2 shows another illustrative embodiment of the present invention in the form of a block diagram.

Although the retardation stage 3 is desirable for inclusion in the circuit as shown in FIG. 1, it is not necessary to the functioning of that circuit. FIG. 2, therefore, illustrates another embodiment of the invention without the retardation stage 3.

Although various modifications may be suggested by those versed in the art, it should be understood that we wish to embody within the scope of the patent granted hereon, all such modifications as reasonably and properly come within the scope of our contribution to the art.

We claim:

1. An apparatus for filtering out baseline fluctuations from physiological measurement signals comprising:
   sampling means operating at a sampling rate for forming sampled values of said measurement signals;
   a first low pass filter connected to an output of said sampling means;
   means connected to an output of said first low pass filter for reducing said sampling rate by a predetermined factor;
   a non-recursive second low pass filter connected to an output of said means for reducing the sampling rate, and having a cut off frequency;
   interpolation means connected to an output of said second low pass filter for increasing said sampling rate by said predetermined factor;
   subtraction means for subtracting the sampled values from said interpolation means from the sampled values of said physiological measurement signal from said sampling means; and
   said first low pass filter being a recursive filter having a frequency range in which phase shifts occur, and having a cut off frequency selected dependent on said cut off frequency of said second low pass filter causing said second low-pass filter to filter out said frequency range.

2. An apparatus as claimed in claim 1, further comprising means for retarding onward transmission of said sampled values from said sampling means to said subtraction means.

* * * * *